(12) United States Patent
Gudimetla et al.

(10) Patent No.: US 12,080,399 B1
(45) Date of Patent: Sep. 3, 2024

(54) HEALTH ANALYSIS BASED ON INGESTIBLE SENSORS

(71) Applicant: CVS Pharmacy, Inc., Woonsocket, RI (US)

(72) Inventors: Dharmendra Gudimetla, Fountain Hills, AZ (US); Karukamaliyil L. Sibin, Allen, TX (US)

(73) Assignee: CVS Pharmacy, Inc., Woonsocket, RI (US)

( * ) Notice: Subject to any disclaimer, the term of this patent is extended or adjusted under 35 U.S.C. 154(b) by 144 days.

(21) Appl. No.: 16/740,049

(22) Filed: Jan. 10, 2020

(51) Int. Cl.
*G16H 20/10* (2018.01)
*G16H 50/30* (2018.01)
*G16H 50/70* (2018.01)

(52) U.S. Cl.
CPC ............ *G16H 20/10* (2018.01); *G16H 50/30* (2018.01); *G16H 50/70* (2018.01)

(58) Field of Classification Search
CPC ........ G16H 20/10; G16H 50/70; G16H 50/30; G16H 10/60; G16H 10/20; G16H 10/40; G16H 10/65; G16H 20/13; G06N 7/01; G06N 7/046
See application file for complete search history.

(56) References Cited

U.S. PATENT DOCUMENTS

| | | | |
|---|---|---|---|
| 8,512,241 B2 | 8/2013 | Bandy et al. | |
| 8,718,193 B2 | 5/2014 | Arne et al. | |
| 8,945,010 B2 | 2/2015 | Semler | |
| 9,235,683 B2 | 1/2016 | Robertson et al. | |
| 9,538,937 B2 | 1/2017 | Rohde et al. | |
| 9,603,550 B2 | 3/2017 | Behzadi | |
| 9,883,819 B2 | 2/2018 | Jensen et al. | |
| 2010/0042329 A1* | 2/2010 | Hood ................. | G01N 33/6803 702/19 |
| 2010/0292634 A1* | 11/2010 | Kircher, Jr. ......... | A61M 5/1723 604/66 |
| 2012/0303388 A1* | 11/2012 | Vishnubhatla ......... | G06V 20/66 705/2 |
| 2016/0106339 A1 | 4/2016 | Behzadi et al. | |
| 2016/0198978 A1* | 7/2016 | Nemoto ............... | A61B 5/7435 600/302 |
| 2016/0324442 A1 | 11/2016 | Zdeblick | |
| 2017/0303818 A1* | 10/2017 | Behzadi ............... | A61B 5/0022 |
| 2018/0272065 A1* | 9/2018 | Talbot ............... | A61M 5/14212 |
| 2018/0322941 A1* | 11/2018 | Krishnan ............... | G16H 40/63 |
| 2018/0330824 A1* | 11/2018 | Athey ................... | G16H 50/20 |

FOREIGN PATENT DOCUMENTS

| CA | 2909033 | 4/2017 |
|---|---|---|
| TW | 201907866 | 3/2019 |

\* cited by examiner

*Primary Examiner* — Chad A Newton
(74) *Attorney, Agent, or Firm* — Patent Law Works, LLP (57) ABSTRACT

A health analysis system and method configured to base sensor measurements on detection of ingestion of a medication by a patient. The health analysis system receives an indicator collected by a first sensor associated to the patient. The indicator identifies a first adherence event at a first indicator time indicating at least a first medication was ingested by the patient. In response to detection of the indicator, first physiological data of the patient is received which was collected by a second sensor. A first wellness indicator is predicted based on the first physiological data of the patient.

19 Claims, 5 Drawing Sheets

HEALTH ANALYSIS BASED ON INGESTIBLE SENSORS

TECHNICAL FIELD

The present disclosure generally relates to health analysis, and more particularly, relates to systems and methods for analyzing physiological conditions in response to ingesting medications.

BACKGROUND

Medications may be prescribed to patients for various conditions, and may cause physiological changes in the patient that may be indicative of medical conditions that may be of importance to the patient and informative to a prescribing physician. Detection of the physiological changes in the patient in response to the ingestion of the medication may be challenging to timely measure to generate informative physiological data relating to the patient. Further, measuring physiological data from a patient may result in useless data when a patient may not have timely or properly medicated.

There is a need therefore to coordinate the measurement of physiological data in a patient with the timing of the efficacy of the medication taken by the patient.

SUMMARY

The present disclosure describes, among other things, various aspects for collecting and processing physiological data from a patient. Various aspects are described which collect vital physiological data from patients, the collection of which coincides with ingesting the medication. The ingested medication includes a sensor that generates an indication that the medication was ingested by the patient. In general, one innovative aspect of the subject matter described in this disclosure may be embodied in a computer-implemented method, comprising: receiving, by a computer system, an indicator collected by a first sensor associated to the patient, the indicator identifying a first adherence event at a first indicator time indicating at least a first medication was ingested by the patient; in response to detection of the indicator, receiving, by the computer system, first physiological data of the patient collected by a second sensor associated with the patient; and predicting, by the computer system, a first wellness indicator of the patient based on the first physiological data of the patient.

Implementations may include one or more of the following features. The method further comprising: comparing, by the computer system, the first physiological data of the patient against peer group data representative of at least one other patient having at least one of a peer group gender, a peer group age, and a peer group race within a range of at least one of a patient gender, a patient age, and a patient race of the patient; and generating, by the computer system, a second wellness indicator of the patient based on the comparison.

The method wherein the comparing the first physiological data of the patient against the peer group data, further comprises: receiving, by the computer system, a second physiological data of the patient collected prior to receiving the indicator by the second sensor associated with the patient; and receiving, by the computer system, a third physiological data of the patient collected after the indicator by the second sensor associated with the patient; and wherein the generating the second wellness indicator of the patient further comprises: predicting a medical condition of the patient based on a comparison of the second physiological data of the patient and the third physiological data of the patient with the peer group data of the at least one other peer patient.

The method further comprising: storing, by the computer system, the first indicator time with a history of the patient. The method further comprising: in response to not receiving a subsequent indicator for the patient at a subsequent time as determined by passing of a subsequent threshold amount of time, generating an alert indicating the patient missed taking at least one of the first medication at the subsequent time; and transmitting the alert to at least one of the patient and a physician of the patient.

The method further comprising: generating a graph of the history of the first physiological data of the patient; and transmitting the graph to at least one of the patient, and a physician of the patient. The method further comprising: augmenting the graph based on comparing the first physiological data of the patient against peer group data representative of at least one other patient having at least one of a peer group gender, a peer group age, and a peer group race within a range of at least one of a patient gender, a patient age, and a patient race of the patient. The method further comprising: receiving, by the computer system, a second physiological data of the patient collected prior to receiving the indicator by the second sensor associated with the patient; receiving, by the computer system, a third physiological data of the patient collected after the indicator by the second sensor associated with the patient; and transmitting, by the computer system, the second physiological data of the patient and the third physiological data of the patient to at least one of the patient and a physician of the patient.

The method further comprising: comparing, by the computing device, the second physiological data of the patient and the third physiological data of the patient; and in response to the comparison of the second physiological data of the patient and the third physiological data of the patient exceeding a normal threshold, transmitting an alert to at least one of the patient and a physician of the patient indicating an abnormal response to the at least one of the first medication. The method further comprising: setting, by the computing device, a before indicator range within which the second physiological data of the patient is anticipated by a physician; setting, by the computing device, an after medication-administration indicator range within which the third physiological data of the patient is anticipated by the physician; and in response to one of the second physiological data of the patient being outside of the before indicator range, or the third physiological data of the patient being outside of the after medication-administration indicator range, transmitting the alert to at least one of the patient and a physician of the patient indicating the abnormal response to the at least one of the first medication.

Another general aspect includes a system comprising: a sensor data management module configured to receive an indicator collected by a first sensor associated to the patient, the indicator identifying a first adherence event at a first indicator time indicating at least a first medication was ingested by the patient; the sensor data management module further configured, in response to detection of the indicator, to receive first physiological data of the patient collected by a second sensor associated with the patient; and a predictive analytics module configured to predict a first wellness indicator of the patient based on the first physiological data of the patient.

Implementations may include one or more of the following features. A system a progress tracking module configured to: compare the first physiological data of the patient against peer group data representative of at least one other patient having at least one of a peer group gender, a peer group age, and a peer group race within a range of at least one of a patient gender, a patient age, and a patient race of the patient; and generate a second wellness indicator of the patient based on the comparison. The system wherein the sensor management module is further configured to: receive a second physiological data of the patient collected prior to receiving the indicator by the second sensor associated with the patient; and receive a third physiological data of the patient collected after the indicator by the second sensor associated with the patient; and wherein the progress tracking module is further configured to: predict a medical condition of the patient based on a comparison of the second physiological data of the patient and the third physiological data of the patient with the peer group data of the at least one other patient.

The system further comprising: a progress tracking module configured to store the first indicator time with a history of the patient. The system further comprising: a sensitive prescription tracking module configured to: in response to not receiving a subsequent indicator for the patient at a subsequent time as determined by passing of a subsequent threshold amount of time, generate an alert indicating the patient missed taking at least one of the first medication at the subsequent time; and transmit the alert to at least one of the patient and a physician of the patient.

The system a pattern-based vital monitoring module configured to: generate a graph of the history of the first physiological data of the patient; and transmit the graph to at least one of the patient, and a physician of the patient. The system wherein the progress tracking module is further configured to: augment the graph based on comparing the first physiological data of the patient against peer group data representative of at least one other patient having at least one of a peer group gender, a peer group age, and a peer group race within a range of at least one of a patient gender, a patient age, and a patient race of the patient.

The system wherein: the sensor data management module is further configured to: receive a second physiological data of the patient collected prior to receiving the indicator by the second sensor associated with the patient; and receive a third physiological data of the patient collected after the indicator by the second sensor associated with the patient; and a sensitive prescription tracking module configured to transmit the second physiological data of the patient and the third physiological data of the patient to at least one of the patient and a physician of the patient. The system wherein the sensitive prescription tracking module further configured to: compare the second physiological data of the patient and the third physiological data of the patient; and in response to the comparison of the second physiological data of the patient and the third physiological data of the patient exceeding a normal threshold, transmit an alert to at least one of the patient and a physician of the patient indicating an abnormal response to the at least one of the first medication.

Another general aspect includes a system comprising: means for receiving, by the computer system, an indicator collected by a first sensor associated to the patient, the indicator identifying a first adherence event at a first indicator time indicating at least a first medication was ingested by the patient; in response to detection of the indicator, means for receiving, by the computer system, first physiological data of the patient collected by a second sensor associated with the patient; and means for predicting, by the computer system, a first wellness indicator of the patient based on the first physiological data of the patient.

It should be understood that the language used in the present disclosure has been principally selected for readability and instructional purposes, and not to limit the scope of the subject matter disclosed herein.

BRIEF DESCRIPTION OF THE DRAWINGS

The present disclosure is illustrated by way of example, and not by way of limitation in the figures of the accompanying drawings in which like reference numerals are used to refer to similar elements.

DETAILED DESCRIPTION

Health analysis systems have utilized surveys or self-reporting from patients to obtain data for creating a health profile from which to provide predictive and preventative guidance to patients, physicians, and other stakeholders. While patients are in the best position to report such data, patient-reported data tends to be subjective and lacks precision for basing objective predictions and providing objective preventative guidance. For example, a patient may report that a medication was taken on a certain day or time, but the effects of the medication may not have been measured, or in the event data was gathered from a patient, the timing of the gathering may not have been synchronized with the activation of the medication resulting in varying and inconsistent data.

Further, a patient may use subjective memory to report data including the taking of the medication and any measurement values reported as data in response to taking the medication. Also, the patient may forget to take the medication and fail to report missing dosages, resulting in the medication having a reduced efficacy on the patient. Also, the patient, out of embarrassment or otherwise, may report compliance of taking the medication, when the medication was in fact skipped. Such a reduced efficacy may result in a prescribing physician unnecessarily increasing the dosage which may be dangerous and even fatal to the patient.

Yet further, the performance of the medication, when taken as prescribed, may perform outside prescribed norms without the prescribing physician receiving any objective feedback about the out-of-range efficacy of the medication. Again, such an improper efficacy may be dangerous and even fatal to the patient. These variables associated with medication administered, or lack thereof, result in inaccurate data which becomes problematic when attempting to provide objective predictive and objective preventative care to a patient and/or other stakeholders of a patient's wellbeing.

Accordingly, a health analysis system and method, described herein, provides for receiving an indicator collected by a first sensor associated to the patient. The indicator identifies a first adherence event at a first indicator time indicating at least a first medication was ingested by the patient. In response to detection of the indicator, first physiological data of the patient collected by a second sensor associated with the patient is received. A first wellness indicator of the patient based on the first physiological data of the patient is then predicted.

Figure 1:
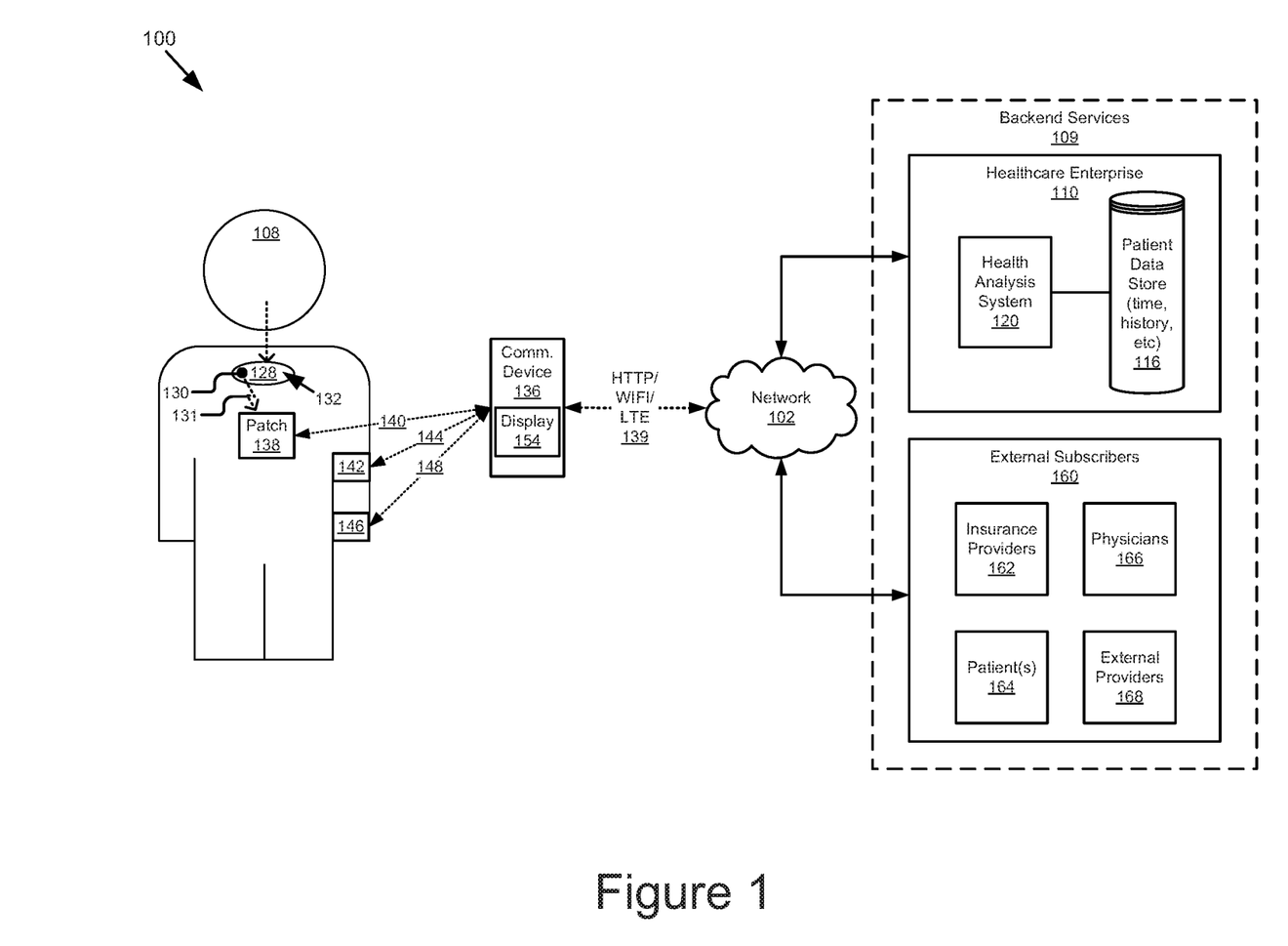
FIG. 1 is a block diagram of an example system for health analysis based on ingested medication tracking.

FIG. 1 is a block diagram of an example system for health analysis based on ingested medication tracking. A health analysis system 100 analyzes the health of the patient 108 by detecting and collecting physiological data from the patient and forwarding the physiological data to a healthcare enterprise 110 for analysis and processing. The healthcare enterprise 110 may analyze the physiological data and compare such data against other stored data related to the patient or to other peer groups to which the patient may belong based on one or more various factors.

The patient 108 may be one of an in-patient or an out-patient that is prescribed one or more medications 128. Further, the medication 128 may be self-administered or may be administered by an attending assistant. While an institution protocol may require manual recording of the medication administration act, the system and method described herein is administration-timing agnostic to any such recordation as such events are objectively detected.

Medication 128 may include an ingestible transmitter 130 in addition to a prescribed pharmaceutical compound 132. The ingestible transmitter 130 may be inert or deactivated during manufacturing and storage of the medication 128. The ingestible transmitter 130 may become activated and transmit an indicator in response to the medication 128 being ingested by the patient 108 followed by the medication 128 becoming exposed to, for example, stomach acids of the patient 108 resulting in switching the ingestible transmitter 130 into an active or transmitting state.

Thereafter, the ingestible transmitter 130 generates and transmits a signal or indicator 131 that is received or detected by a sensor 138. The sensor 138, for example in the form of a patch, may be attached to or associated with the patient 108 in such a manner as to detect the indicator 131 which is indicative of an objective level of dispersion of the medication 128 following ingestion by the patient 108. Accordingly, the indicator 131 provides an affirmative indication that the medication 128 was ingested by the patient 108 and provides an objective time-based indication or time-stamp from which to obtain physiological data from the patient 108. Accordingly, the obtained physiological data is objectively timed to the dispersion of the prescribed pharmaceutical compound 132 of the medication 128.

The sensor 138 may include a receiver configured to monitor for and receive the indicator 131 and a transceiver configured to notify a communication device 136 over a communication link 140 of the occurrence or detection of the indicator 131. The communication link 140 may be configured according to various protocols, and example of which may be a Bluetooth Low Energy (BLE) link.

The communication device 136 may be configured as a smart phone, other portable device, or may be configured as a fixed communication device. The communication device 136 may include a display 154 through which information may be exchanged with the patient 108. The communication device 136 is further configured to communicate the occurrence of the indicator 131 with backend services 109 such as a healthcare enterprise 110 and/or other stakeholders such as external subscribers 160. Communication between the communication device 136 and the backend services may occur over one or more communication links, an example of which is illustrated as a wireless link 139 coupled to an accessible network 102, and example of which may be a wide area network such as the Internet.

The backend services 109 may respond to the receipt of indicator 131 and communicate requests for other sensor data to the communication device 136. Additionally, backend services 109 may log and track the ingestion of the medication 128 based upon receipt of the indicator 131.

Additional sensors such as a second sensor 142 and/or third sensor 146 may also be attached to or associated with the patient 108 to measure and acquire physiological data of the patient. By way of example, sensor 142 may be configured to measure the blood pressure of the patient 108 and communicate the measured blood pressure over a communication link 144 to the communication device 136. The communication device 136 may thereafter relay the physiological data corresponding to the blood pressure measurement to the backend services 109 for analysis and/or for storage. Also by way of example, sensor 146 may be configured to obtain further physiological data in the form of white blood cell counts. Such physiological data may likewise be communicated to the backend services 109 over a communication link 148 and via the communication device 136.

It should be noted that the measurement of physiological data by way of other sensors such as sensor 142 and sensor 146 may be requested or coordinated in response to receipt of the indicator 131. Alternatively, the communication device 136 may be configured to provide timing of the measurement of physiological data from additional sensors, such as sensor 142 and/or sensor 146, with the timing coinciding with or having an offset (including earlier or later in time) to the detected indicator 131. The physiological data is then forwarded to the backend services 109 for processing and storage.

The backend services 109 may predict a wellness indicator of the patient based on the received physiological data of the patient. Further, the backend services 109 may utilize previously received and stored physiological data to predict a wellness indicator of the patient. Yet further, backend services 109 may utilize physiological data of peer groups of the patient in order to predict a wellness indicator of the patient.

A healthcare enterprise 110 may include a health analysis system 120 and a storage system such as patient data store 116 to accomplish the mentioned wellness predictions. The health analysis system 120 may compare the physiological data of the patient against peer group data that is stored in storage system such as patient data store 116 which is representative of one or more other patients having at least a peer or group characteristic of the patient. Such peer group characteristics may be one or more of a peer group gender, a peer group age, a peer group race which corresponds to or is within a range of the patient's gender, the patient age, and the patient race. A wellness indicator of the patient may then be generated based upon such peer group comparisons.

Further the comparing of the physiological data of the patient against the peer group data may further include receiving second or additional physiological data of the patient collected prior to receipt of the indicator 131 by an additional or second sensor. Third or additional physiological data of the patient may be collected after receipt of the indicator 131 from the additional or second sensor coupled to the patient. Accordingly, a wellness indicator of the patient may be generated by predicting a medical condition of the patient based on a comparison of the second physiological data of the patient and the third physiological data of the patient, with peer or group data of one or more other patient.

Further, preventative medication tracking may also be performed by storing a time associated with the indicator 131 in a history of the patient. Further, in response to the health analysis system 120 not receiving a subsequent indicator for the patient at a subsequent time as determined by the passage of a subsequent threshold amount of time, the health analysis system 120 may generate an alert indicating that the at least one medication and a subsequent scheduled time. The alert may be transmitted to one or more of various stakeholders including to the patient who may receive the alert on the communication device 136, or to a physician which may be associated with an entity in the backend services 109.

Further, the health analysis system 120 may generate a graph of the history of the physiological data of the patient and transmit the graph to the communication device 136 and/or a physician that may be associated with the backend services 109. Yet further, the graph may be augmented based on comparing physiological data of the patient against peer or group data representative of at least one other patient having at least one of a peer group gender, a peer group age, and a peer group race corresponding to or within a range of at least one of the patient's gender, the patient's age, and the patient's race.

In other embodiments, the patient's sensitivity to medication may be tracked by measuring the patient using a sensor prior to ingesting the medication and subsequently measuring the patient using the sensor following administration of the medication to the patient. Specifically, physiological data of the patient may be received as collected prior to the generation of the indicator 131 and physiological data of the patient may be collected and received after the generation of the indicator 131. Both of the physiological data of the patient may thereafter be transmitted to the backend services 109, and more specifically to a prescribing physician of the patient to determine the efficacy of the medication 128 with respect to the patient 108.

In other embodiments, the backend services 109 may establish patterns or ranges about which received physiological data may be compared. When the physiological data is outside of acceptable ranges, the backend services 109 may notify the patient, prescribing physician, or other stakeholders in the patient's well-being. Specifically, an acceptable range for a patient's physiological data which is acceptable prior to administration of the medication may be established by an entity such as a prescribing physician. Similarly, an acceptable range for patient's physiological data which is acceptable after administration of the medication may be established by an entity such as a prescribing physician. When the actual physiological data of the patient is received, it is compared against the various ranges and, when found to be out of the acceptable range, the health analysis system 120 may notify one or more of the patient, and a physician of the patient.

As stated, backend services 109 may further include external subscribers 160. External subscribers may be stakeholders in the patient's well-being and may include insurance providers 162, patient or patients 164, physicians 166, and external providers 168. These external subscribers 160 may monitor a patient's physiological data and may provide predictive and/or preventative plans or information to the patient 108.

Figure 2:
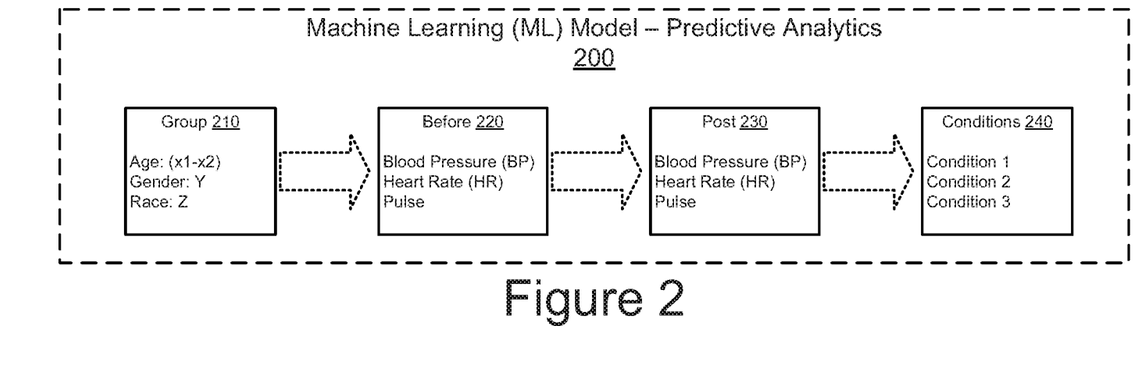
FIG. 2 illustrates a flow diagram of predictive analysis using a health analysis system.

FIG. 2 illustrates a flow diagram of predictive analysis using a health analysis system. The illustrated predictive analysis may be embedded within the health analysis system 120 of FIG. 1. The predictive analysis may be implemented using predictive analytics embodied in a machine learning model 200. The machine learning model 200 may use machine learning techniques, data mining techniques, and/or predictive modeling techniques. The machine learning model 200 may receive and include a peer group data 210. The peer group data 210 may be based on various peer group characteristics, examples of which may include gender, age, and race.

Accordingly, a patient's characteristics may be compared against those of a peer group. For example, a block 220 may receive a patient's physiological data including blood pressure, heart rate, and pulse, at a time that occurs prior to the occurrence of the indicator 131. Block 220 may compare those values of the patient's physiological data occurring prior to the occurrence of the indicator 131 against physiological data of others in a peer group to determine whether the values are within acceptable ranges as described above.

A block 230 may receive a patient's physiological data including blood pressure, heart rate, and pulse, at a time that occurs after the occurrence of the indicator 131. Block 230 may compare those values of the patient's physiological data occurring after the occurrence of the indicator 131 against physiological data of others in the peer group to determine whether the values are within acceptable ranges as described above.

Based upon the findings in block 220 and block 230, a block 240 generates outputs or conditions representative of conditions corresponding to the relationships identified in block 220 and block 230. The identified conditions as determined by a machine learning model 200 in the health analysis system 120 may be reported back to the patient 108, and/or other stakeholders interested in the patient's well-being. Information that may be reported back include results of medication tracking and alerts based upon physiological data being outside of ranges or missed medication dosages. Furthermore, the machine learning models may generate progress and wellness graphs provided to a display 154 on the communication device 136 which may be readily accessible to the patient 108.

Figure 3:
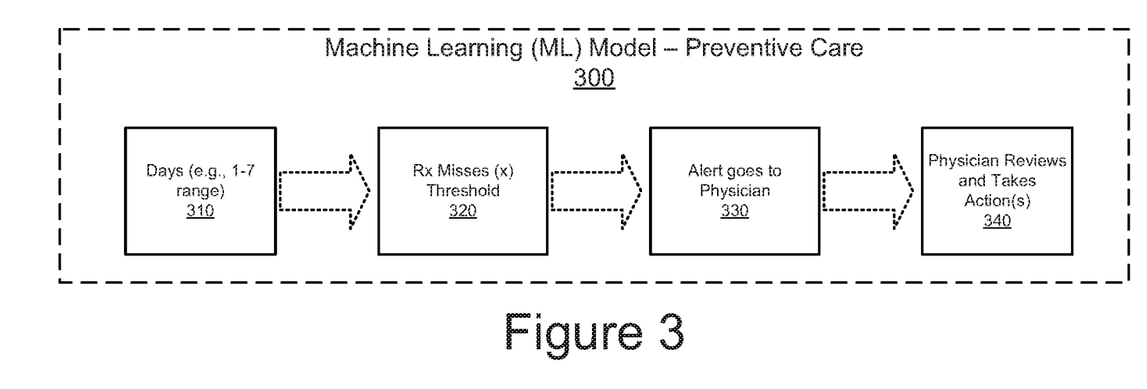
FIG. 3 illustrates a flow diagram of preventative care using a health analysis system.

FIG. 3 illustrates a flow diagram of preventive care using a health analysis system. The illustrated preventative analysis may be embedded with in the health analysis system 120 of FIG. 1. The preventative care analysis may be implemented using preventative analytics embodied in a machine learning model 300. The machine learning model 300 may use machine learning techniques, data mining techniques, and/or predictive modeling techniques. The machine learning model 300 may include an individual tracking block 310. The individual tracking block 310 may include a history of medication ingestion by the patient.

In a block 320, the machine learning model 300 identifies a quantity of skipped or otherwise missed administration opportunities for the medication. A patient's progress may also be tracked along with a comparison of the patient's physiological data with other peer group physiological data.

In a block 330, an alert may be generated when a patient's physiological data is determined to be outside of acceptable ranges. The alert may be sent to a prescribing physician and/or the patient.

In a block 340, an entity, such as a prescribing physician, upon receiving the alert may take action such as modifying the patient's medication including dosages and periodicity of administration of the medication.

Figure 4A:
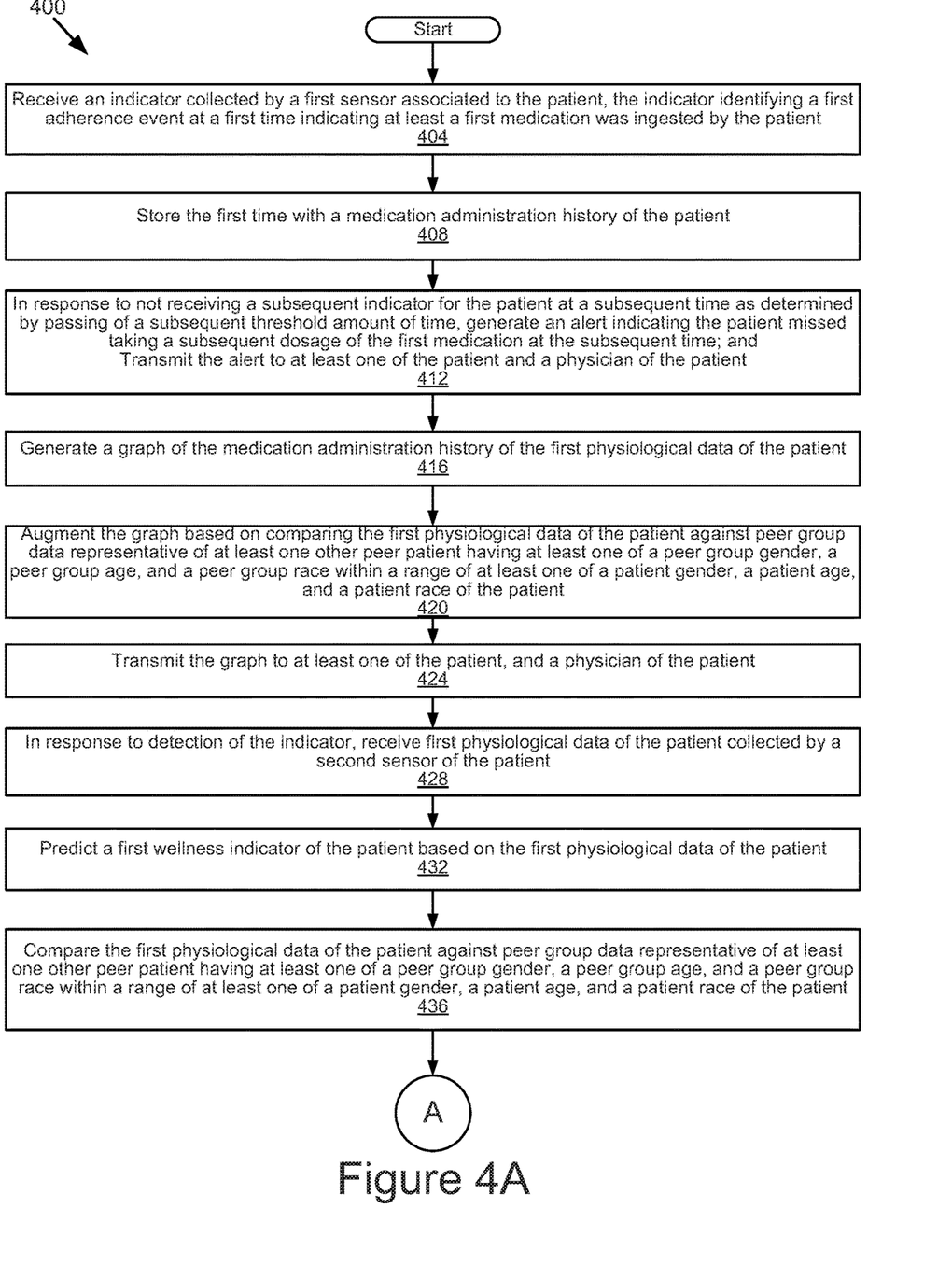
FIGS. 4A and 4B are flowcharts of example methods for predictive and preventative care using a health analysis system.
Figure 4B:
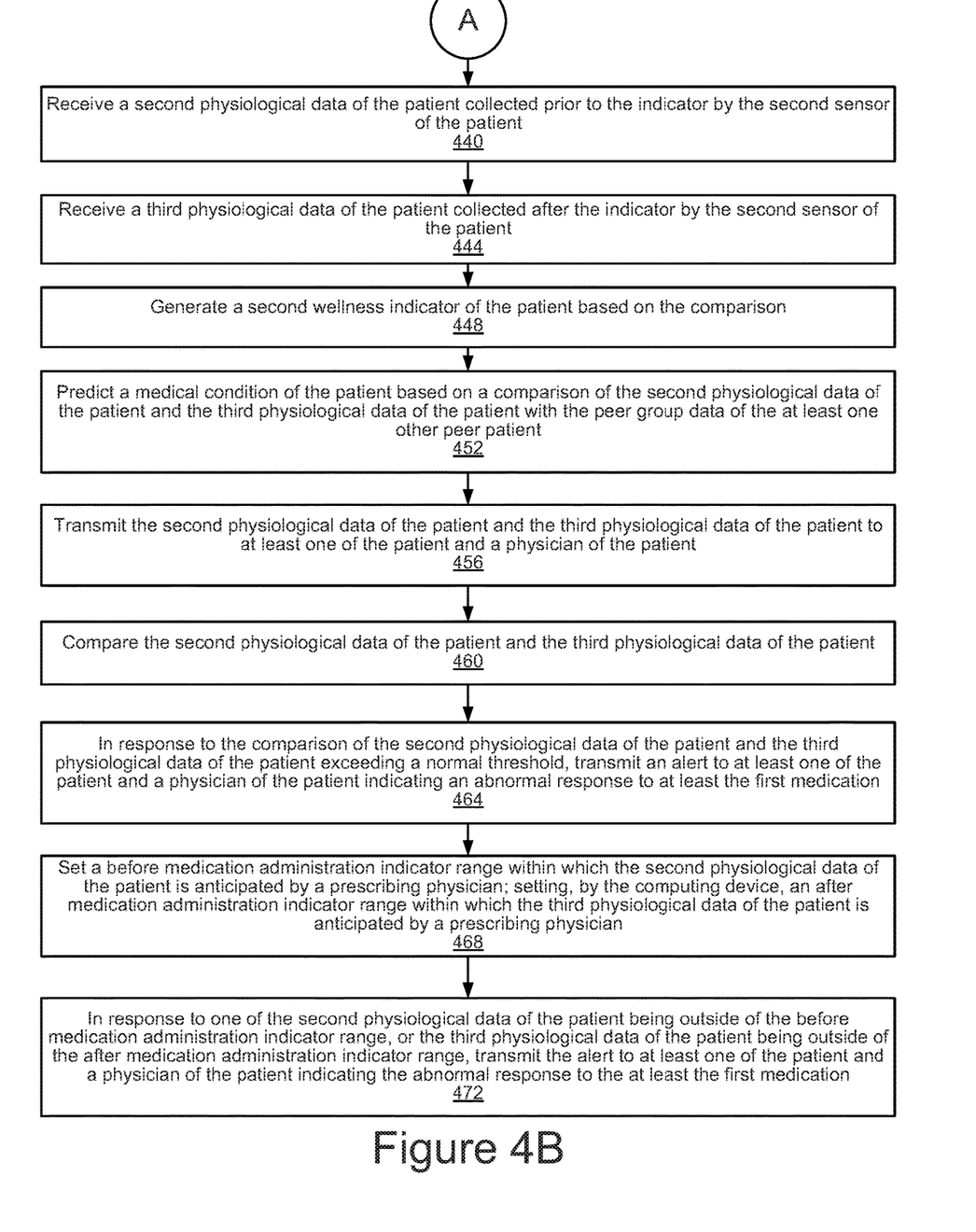

FIG. 4A and FIG. 4B are flowcharts of example methods for predictive and preventative care using a health analysis system. The flowchart of FIG. 4B is a continuation of the flowchart 400 of FIG. 4A. The flowchart 400 generates a wellness indicator based on the measured vitals of the patient based on an objective time indicator.

In a block 404, an indicator 131 is received were the indicator is collected by a first sensor 138 associated to the patient 108. The indicator 131 identifies a first adherence event at a first indicator time indicating at least a first medication 128 was ingested by the patient.

In a block 408, the first indicator time associated with the indicator 131 may be stored in a medication administration history of the patient as stored in the patient data store 116. The medication administration history may include one or more data entries corresponding to the detection of previous or subsequent indicators 131 of the patient, and may include designations of missed dosages of prescribed medication 128.

In a block 412, in response to not receiving a subsequent indicator 131 for the patient at a subsequent time as determined by the passing of a subsequent threshold amount of time, an alert is generated indicating that the patient missed taking or ingesting a dosage of the first medication at the subsequent time. The alert may be transmitted to one or more of the patient and a physician of the patient, or to other stakeholders in the patient's wellbeing.

In a block 416, a graph of the medication administration history of the first physiological data of the patient 108 may be generated.

In a block 420, the graph of the medication administration history may be augmented by comparing the first physiological data of the patient against peer group data representative of at least one other patient having at least one of a peer group gender, a peer group age, and a peer group race that is within a range of at least one of the patient's gender, the patient's age, and the patient's race.

In a block 424, the graph may be transmitted to at least one of the patient, a physician, or to other stakeholders in the patient's wellbeing.

In a block 428, in response to detection of the indicator 131, the first physiological data of the patient collected by a second sensor 142 of the patient may be received.

In a block 432, a first wellness indicator of the patient based on the first physiological data of the patient is predicted.

In a block 436, the first physiological data of the patient may be compared against peer group data representative of at least one other peer patient having at least one of a peer group gender, a peer group age, and a peer group race within a range of the patient gender, the patient age, and the patient race.

In a block 440, a second physiological data of the patient collected prior to generation of the indicator 131 may be received as detected by the second sensor 142 associated with the patient 108.

In a block 444, a third physiological data of the patient may be received. The third physiological data of the patient may be collected after generation of the indicator 131 with the third physiological data of the patient being detected by the second sensor 142.

In a block 448, a second wellness indicator of the patient may be generated and may be based upon the comparison.

In a block 452, a medical condition of the patient may be predicted based on a comparison of the second physiological data of the patient and the third physiological data of the patient. The comparison may be performed against the peer group data of at least one other peer patient.

In a block 456, the second physiological data and the third physiological data of the patient may be transmitted to at least one of the patient and a physician such as an attending physician or a prescribing physician.

In a block 460, the second physiological data of the patient and the third physiological data of the patient may be compared.

In a block 464, in response to the comparison of the second physiological data of the patient and the third physiological data of the patient exceeding a normal threshold, an alert may be transmitted to at least one of the patient and a physician such as an attending physician or a prescribing physician indicating an abnormal response to the first medication.

In a block 468, a before medication-administration indicator range may be set within which the second physiological data of the patient is anticipated by a prescribing physician. Also, and after medication-administration indicator range may be set within which the third physiological data of the patient is anticipated by the prescribing physician.

In a block 472, in response to one of the second physiological data of the patient being outside of the before medication-administration range, or the third physiological data of the patient being outside of the after medication-administration indicator range, transmitting the alert to at least one of the patient and a physician of the patient indicating the abnormal response to the first medication.

Figure 5:
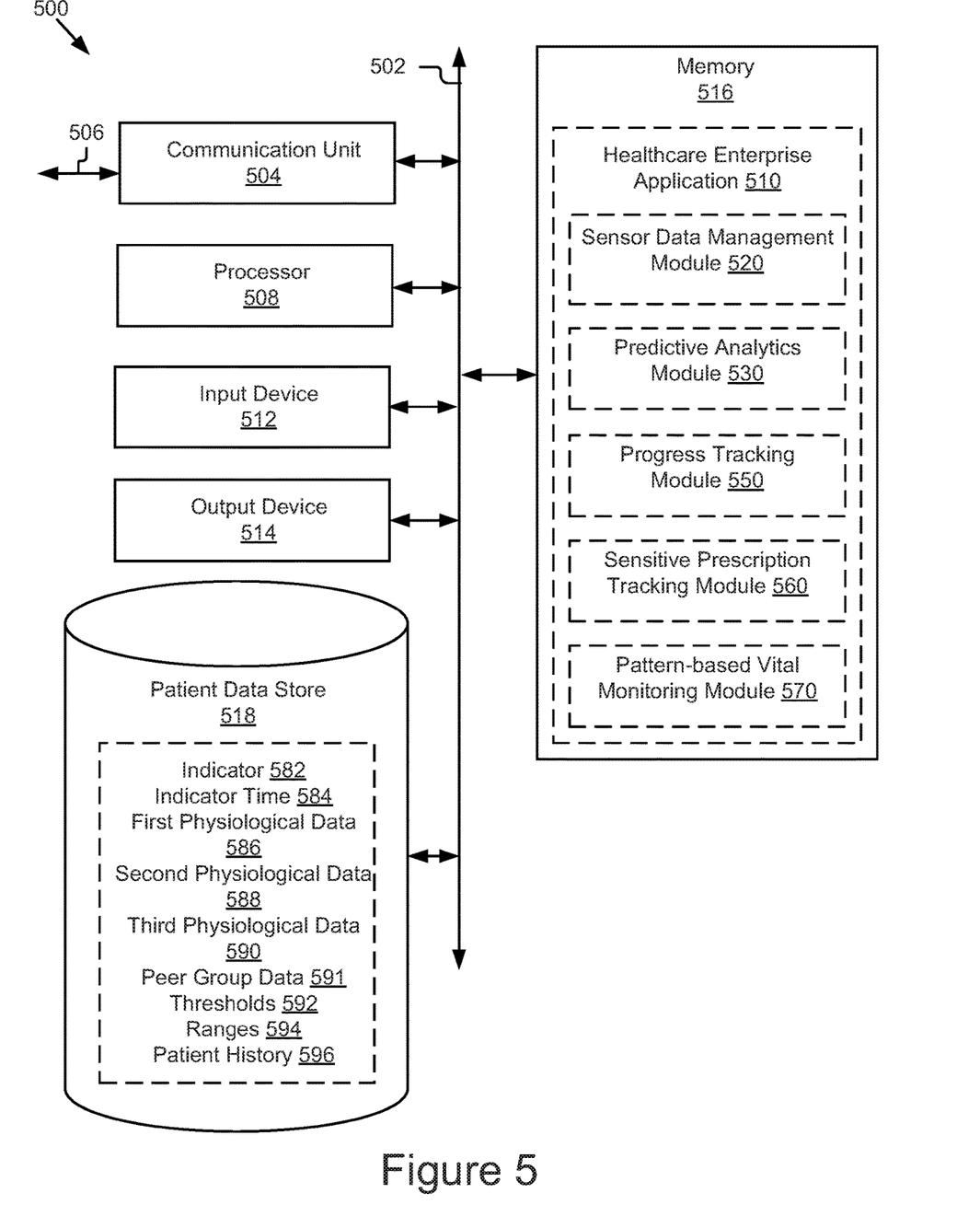
FIG. 5 is a block diagram of an example health analysis system.

FIG. 5 is a block diagram of an example health analysis system, which may represent a computing device configured to implement modules depicted in FIG. 1, such as healthcare enterprise 110, including health analysis system 120 and patient data store 116, depending on the implementation.

As depicted, the computing system 500 may include a processor 508, a memory 516, a communication unit 504, an output device 514, an input device 512, and a patient data store 518, which may be communicatively coupled by a communication bus 502. The computing system 500 depicted in FIG. 5 is provided by way of example and it should be understood that it may take other forms and include additional or fewer components without departing from the scope of the present disclosure. For instance, various components of the computing device may be coupled for communication using a variety of communication protocols and/or technologies including, for instance, communication buses, software communication mechanisms, computer networks, etc. While not shown, the computing system 500 may include various operating systems, sensors, additional processors, and other physical configurations. The processor 508, memory 516, communication unit 504, etc., are representative of one or more of these components.

The processor 508 may execute software instructions by performing various input, logical, and/or mathematical operations. The processor 508 may have various computing architectures to method data signals (e.g., CISC, RISC, etc.). The processor 508 may be physical and/or virtual, and may include a single core or plurality of processing units and/or cores. In some implementations, the processor 508 may be coupled to the memory 516 via the bus 502 to access data and instructions therefrom and store data therein. The bus 502 may couple the processor 508 to the other components of the computing system 500 including, for example, the memory 516, the communication unit 504, the input device 512, the output device 514, and the patient data store 518.

The memory 516 may store and provide data access to the other components of the computing system 500. The memory 516 may be included in a single computing device or a plurality of computing devices. In some implementations, the memory 516 may store instructions and/or data that may be executed by the processor 508. For example, the memory 516 may store a healthcare enterprise application 510. The memory 516 is also capable of storing other instructions and data, including, for example, an operating system, hardware drivers, other software applications, databases, etc. The memory 516 may be coupled to the bus 502 for communication with the processor 508 and the other components of computing system 500.

In the example shown, healthcare enterprise application 510 includes a plurality of modules related to the operation of healthcare enterprise application 510 in accordance with the systems and methods described above. These modules are shown by example and may not include all modules in the healthcare enterprise application 510. Healthcare enterprise application 510 may include sensor data management module 520 for receiving an indicator collected by a first sensor associated to the patient. The indicator identifies a first adherence event at a first indicator time indicating at least a first medication was ingested by the patient. The sensor data management module is further configured, in response to detection of the indicator, to receive first physiological data of the patient collected by a second sensor associated with the patient.

The sensor data management module 520 is further configured to receive a second physiological data of the patient collected prior to receiving the indicator by the second sensor associated with the patient and receive a third physiological data of the patient collected after the indicator by the second sensor associated with the patient.

Healthcare enterprise application 510 further includes a predictive analytics module 530. Predictive analytics module 530 is configured to predict a first wellness indicator of the patient based on the first physiological data of the patient.

Healthcare enterprise application 510 further includes a progress tracking module 550. The progress tracking module 550 is configured to compare the first physiological data of the patient against peer group data representative of at least one other peer group patient having at least one of the peer group gender, a peer group age, and a peer group race within a range of at least one of the patient gender, a patient age, and the patient race. The progress tracking module 550 is further configured to generate a second wellness indicator of the patient based on the comparison.

The progress tracking module 550 is further configured to predict a medical condition of the patient based on a comparison of the second physiological data of the patient and the third physiological data of the patient with the peer group data of at least one other peer patient. The progress tracking module 550 is further configured to store the first indicator time with the medication administration history of the patient.

Healthcare enterprise application 510 further includes a sensitive prescription tracking module 560. Sensitive prescription tracking module 560 is configured to, in response to not receiving a subsequent indicator for the patient at a subsequent time as determined by the passing of a subsequent threshold amount of time, generate an alert indicating the patient missed taking a subsequent dosage of the first medication at the subsequent time. The sensitive prescription tracking module 560 is further configured to transmit the alert to at least one of the patient and a physician, such as an attending physician or a prescribing physician, or other stakeholders in the patient's wellbeing.

Healthcare enterprise application 510 further includes a pattern-based vital monitoring module 570. Pattern-based vital monitoring module 570 is configured to generate a graph of the medication administration history of the first physiological data of the patient. The pattern-based vital monitoring module 570 is further configured to transmit the graph to at least one of the patient and a physician of the patient, such as an attending physician or a prescribing physician, or other stakeholders in the patient's wellbeing.

Further, the progress tracking module 550 may be further configured to augment the graph based on comparing the first physiological data of the patient against peer group data representative of at least one other peer patient having at least one of a peer group gender, a peer group age, and a peer group race within a range of at least one of the patient gender, the patient age, and the patient race.

Further, the sensor data management module 520 may be configured to receive a second physiological data of the patient collected prior to receiving the indicator by the second sensor associated with the patient, and receive a third physiological data of the patient collected after the indicator by the second sensor associated with the patient. Further, the sensitive prescription tracking module 560 may be further configured to transmit the second physiological data of the patient and the third physiological data of the patient to at least one of the patient and a physician of the patient, or other stakeholders in the patient's wellbeing.

The sensitive prescription tracking module 560 may be further configured to compare the second physiological data of the patient and the third physiological data of the patient and, in response to the comparison of the second physiological data of the patient and the third physiological data of the patient exceeding a normal threshold, transmit an alert to at least one of the patient and a physician of the patient, or other stakeholders in the patient's wellbeing. The alert indicating an abnormal response to the first medication.

The patient data store 518 may store various patient data including histories of patient data. For example, patient data store 518 may include storage for indicators 582 corresponding to the received indicators 131, and corresponding indicator times 584. The patient data store 518 may further store first physiological data 586, second physiological data 588, and third physiological data 590. The patient data store 518 may further store or access peer group data as described herein. Patient data store 518 may further include thresholds 592 and ranges 594 used in comparison of values of physiological data including comparisons of peer group data. Patient data store 518 may further include patient history or histories 596 as described herein.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

To ease description, some elements of the system and/or the methods are referred to using the labels first, second, third, etc. These labels are intended to help to distinguish the elements but do not necessarily imply any particular order or ranking unless indicated otherwise.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Various implementations described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of a hardware implementation, a software implementation, or implementations containing both hardware and software elements. For instance, the technology may be implemented in software, which includes but is not limited to firmware, resident software, microcode, etc. Furthermore, the technology can take the form of a computer program object accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and Modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), WebSocket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats. Furthermore, the modules, routines, features, attributes, methodologies and other aspects of the disclosure can be implemented as software, hardware, firmware, or any combination of the foregoing. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment.

The invention claimed is:

1. A computer-implemented method, comprising:
automatically switching, by an ingestible transmitter, from a deactivated state into a transmitting state responsive to exposure to stomach acid of a patient, the ingestible transmitter associated with a first medication ingested by the patient, the ingestible transmitter deactivated during manufacturing of the ingestible transmitter;
transmitting, by an ingestible transmitter to a computer system, an indicator responsive to ingestion of the first medication by the patient and exposure to the stomach acid;
collecting, by a first sensor associated with the patient, the indicator, the indicator identifying a first adherence event at a first indicator time indicating at least the first medication was ingested by the patient;
receiving, by a computer system, the indicator, the indicator collected from the ingestible transmitter and by the first sensor associated with the patient, the indicator identifying the first adherence event at the first indicator time indicating at least the first medication was ingested by the patient, the first medication associated with the ingestible transmitter, and the ingestible transmitter automatically transmitting the indicator responsive to ingestion of the first medication by the patient;
collecting, by a second sensor associated with the patient, physiological data of the patient including first physiological data collected after the indicator and second physiological data collected prior to the indicator;
in response to detection of the indicator, receiving, by the computer system, the first physiological data of the patient collected, by the second sensor associated with the patient, after the indicator;
receiving, by the computer system, the second physiological data collected, by the second sensor associated with the patient, prior to the indicator;
determining, by the computer system, a history of medication ingested by the patient based on receipt of indicators associated with one or more adherence events, wherein the history of medication ingested by the patient indicates whether first medication was taken as prescribed or whether one or more doses were missed;
determining, by the computer system, a medication administration history of the physiological data of the patient based on the history of the medication ingested by the patient, the first physiological data, and the second physiological data; and
predicting, by the computer system and based on a comparison of the medication administration history of the physiological data of the patient to peer group data, a medical condition of the patient and an out-of-range efficacy, wherein:
the peer group data includes one or more medication administration histories associated with one or more peer patients comprising a peer group;
one or more of the peer group data and the medication administration history of the physiological data of the patient include at least one missed dose, thereby including at least one instance where the first medication was not taken as prescribed; and
the out-of-range efficacy is a degree to which the first medication effects a physiological response of the patient, when taken as prescribed, that is outside of a normal range.

2. The computer-implemented method of claim 1, wherein
the peer group data is representative of at least one other peer patient having at least one of a peer group gender, a peer group age, and a peer group race within a range of at least one of a patient gender, a patient age, and a patient race of the patient.

3. The computer-implemented method of claim 1, further comprising:
storing, by the computer system, the first indicator time with a medication administration history of the patient.

4. The computer-implemented method of claim 3, further comprising:
in response to not receiving a subsequent indicator for the patient at a subsequent time as determined by passing of a subsequent threshold amount of time, generating an alert indicating the patient missed taking a subsequent dosage of the first medication at the subsequent time; and
transmitting the alert to at least one of the patient and a physician of the patient.

5. The computer-implemented method of claim 3, further comprising:
generating a graph of the medication administration history of the first physiological data of the patient; and
transmitting the graph to at least one of the patient, and a physician of the patient.

6. The computer-implemented method of claim 5, further comprising:
augmenting the graph based on comparing the first physiological data of the patient against peer group data representative of at least one other peer patient having at least one of a peer group gender, a peer group age, and a peer group race within a range of at least one of a patient gender, a patient age, and a patient race of the patient.

7. The computer-implemented method of claim 1, further comprising:
transmitting, by the computer system, the first physiological data of the patient and the second physiological data of the patient to at least one of the patient and a physician of the patient.

8. The computer-implemented method of claim 7, further comprising:
comparing, by the computing system, the first physiological data of the patient and the second physiological data of the patient; and
in response to the comparison of the first physiological data of the patient and the second physiological data of the patient exceeding a normal threshold, transmitting an alert to at least one of the patient and the physician of the patient indicating an abnormal response to at least one of the first medication.

9. The computer-implemented method of claim 8, further comprising:
setting, by the computing system, a before medication-administration indicator range within which the second physiological data of the patient is anticipated by a physician;
setting, by the computing system, an after medication-administration indicator range within which the first physiological data of the patient is anticipated by the physician; and
in response to one of the second physiological data of the patient being outside of the before medication-administration indicator range, or the first physiological data of the patient being outside of the after medication-administration indicator range, transmitting the alert to at least one of the patient and the physician of the patient indicating the abnormal response to the at least one of the first medication.

10. A system, comprising:

means for automatically switching, by an ingestible transmitter, from a deactivated state into a transmitting state responsive to exposure to stomach acid of a patient, the ingestible transmitter associated with a first medication ingested by the patient, the ingestible transmitter deactivated during manufacturing of the ingestible transmitter;

means for transmitting, by an ingestible transmitter, an indicator responsive to ingestion of the first medication by the patient and exposure to the stomach acid;

means for collecting, by a first sensor associated with the patient, the indicator, the indicator identifying a first adherence event at a first indicator time indicating at least the first medication was ingested by the patient;

means for collecting, by a second sensor associated with the patient, physiological data of the patient including first physiological data collected after the indicator and second physiological data collected prior to the indicator;

means for receiving, by a computer system, the indicator, the indicator collected from the ingestible transmitter and by the first sensor associated with the patient, the indicator identifying the first adherence event at the first indicator time indicating at least the first medication was ingested by the patient, the first medication associated with the ingestible transmitter, and the ingestible transmitter automatically transmitting the indicator responsive to ingestion of the first medication by the patient;

in response to detection of the indicator, means for receiving, by the computer system, the first physiological data of the patient collected by the second sensor associated with the patient, after the indicator;

means for receiving, by the computer system, the second physiological data collected, by the second sensor associated with the patient, prior to the indicator;

means for determining a history of medication ingested by the patient based on receipt of indicators associated with one or more adherence events, wherein the history of medication ingested by the patient indicates whether first medication was taken as prescribed or whether one or more doses were missed;

means for determining a medication administration history of the physiological data of the patient based on the history of the medication ingested by the patient, the first physiological data, and the second physiological data; and means for predicting, by the computer system and based on a comparison of the medication administration history of the physiological data of the patient to peer group data, a medical condition of the patient and an out-of-range efficacy, wherein:

the peer group data includes one or more medication administration histories associated with one or more peer patients comprising a peer group;

one or more of the peer group data and the medication administration history of the physiological data of the patient include at least one missed dose, thereby including at least one instance where the first medication was not taken as prescribed; and the out-of-range efficacy is a degree to which the first medication effects a physiological response of the patient, when taken as prescribed, that is outside of a normal range.

11. A system comprising:

an ingestible transmitter, the ingestible transmitter automatically switching from a deactivated state into a transmitting state responsive to exposure to stomach acid of a patient, the ingestible transmitter associated with a first medication ingested by the patient, the ingestible transmitter deactivated during manufacturing of the ingestible transmitter, and the ingestible transmitter transmitting an indicator responsive to ingestion of the first medication by a patient;

a first sensor associated with the patient, the first sensor collecting the indicator, the indicator identifying a first adherence event at a first indicator time indicating at least the first medication was ingested by the patient;

a second sensor associated with the patient, the second sensor collecting physiological data of the patient including first physiological data collected after the indicator and second physiological data collected prior to the indicator;

one or more processors; and a memory storing instructions that, when executed by the one or more processors, cause the system to:

receive the indicator, the indicator collected from the ingestible transmitter and by the first sensor associated to the patient, the indicator identifying the first adherence event at the first indicator time indicating at least the first medication was ingested by the patient, the first medication associated with the ingestible transmitter, and the ingestible transmitter automatically transmitting the indicator responsive to ingestion of the first medication by the patient;

in response to detection of the indicator, receive the first physiological data of the patient collected, by the second sensor associated with the patient, after the indicator;

receive the second physiological data collected, by the second sensor associated with the patient, prior to the indicator;

determine a history of medication ingested by the patient based on receipt of indicators associated with one or more adherence events, wherein the history of medication ingested by the patient indicates whether first medication was taken as prescribed or whether one or more doses were missed;

determine a medication administration history of the physiological data of the patient based on the history of the medication ingested by the patient, the first physiological data, and the second physiological data; and predict, based on a comparison of the medication administration history of the physiological data of the patient to peer group data, a medical condition of the patient and an out-of-range efficacy, wherein:

the peer group data includes one or more medication administration histories associated with one or more peer patients comprising a peer group;

one or more of the peer group data and the medication administration history of the physiological data of the patient include at least one missed dose, thereby including at least one instance where the first medication was not taken as prescribed; and the out-of-range efficacy is a degree to which the first medication effects a physiological response of the patient, when taken as prescribed, that is outside of a normal range.

12. The system of claim 11, wherein the peer group data is representative of at least one other peer patient having at least one of a peer group gender, a peer group age, and a peer group race within a range of at least one of a patient gender, a patient age, and a patient race of the patient.

13. The system of claim 11, comprising instructions that, when executed by the one or more processors, cause the system to:
   store the first indicator time with a medication administration history of the patient.

14. The system of claim 13, comprising instructions that, when executed by the one or more processors, cause the system to:
   in response to not receiving a subsequent indicator for the patient at a subsequent time as determined by passing of a subsequent threshold amount of time, generate an alert indicating the patient missed taking a subsequent dosage of the first medication at the subsequent time; and
   transmit the alert to at least one of the patient and a physician of the patient.

15. The system of claim 13, comprising instructions that, when executed by the one or more processors, cause the system to:
   generate a graph of the medication administration history of the first physiological data of the patient; and
   transmit the graph to at least one of the patient, and a physician of the patient.

16. The system of claim 15, comprising instructions that, when executed by the one or more processors, cause the system to:
   augment the graph based on comparing the first physiological data of the patient against peer group data representative of at least one other peer patient having at least one of a peer group gender, a peer group age, and a peer group race within a range of at least one of a patient gender, a patient age, and a patient race of the patient.

17. The system of claim 11, comprising instructions that, when executed by the one or more processors, cause the system to:
   transmit the first physiological data of the patient and the second physiological data of the patient to at least one of the patient and a physician of the patient.

18. The system of claim 17, comprising instructions that, when executed by the one or more processors, cause the system to:
   compare the first physiological data of the patient and the second physiological data of the patient; and
   in response to the comparison of the first physiological data of the patient and the second physiological data of the patient exceeding a normal threshold, transmit an alert to at least one of the patient and the physician of the patient indicating an abnormal response to at least one of the first medication.

19. The system of claim 18, comprising instructions that, when executed by the one or more processors, cause the system to:
   set a before medication-administration indicator range within which the second physiological data of the patient is anticipated by a physician;
   set an after medication-administration indicator range within which the first physiological data of the patient is anticipated by the physician; and
   in response to one of the second physiological data of the patient being outside of the before medication-administration indicator range, or the first physiological data of the patient being outside of the after medication-administration indicator range, transmit the alert to at least one of the patient and the physician of the patient indicating the abnormal response to the at least one of the first medication.

* * * * *